(12) United States Patent
Walsh et al.

(10) Patent No.: US 9,660,626 B2
(45) Date of Patent: May 23, 2017

(54) IMPLANTABLE MEDICAL DEVICE HAVING CLOCK TREE NETWORK WITH REDUCED POWER CONSUMPTION

(71) Applicant: Medtronic, Inc., Minneapolis, MN (US)

(72) Inventors: Kevin K. Walsh, Peoria, AZ (US); Melvin P. Roberts, Chandler, AZ (US)

(73) Assignee: Medtronic, Inc., Minneapolis, MN (US)

( * ) Notice: Subject to any disclaimer, the term of this patent is extended or adjusted under 35 U.S.C. 154(b) by 430 days.

(21) Appl. No.: 13/802,877

(22) Filed: Mar. 14, 2013

(65) Prior Publication Data

US 2014/0276664 A1 Sep. 18, 2014

(51) Int. Cl.
*H03K 3/00* (2006.01)
*H03K 5/15* (2006.01)
*G06F 1/10* (2006.01)
*A61M 5/142* (2006.01)

(52) U.S. Cl.
CPC ............ *H03K 5/1504* (2013.01); *G06F 1/10* (2013.01); *A61M 5/14276* (2013.01); *A61M 2205/8212* (2013.01)

(58) Field of Classification Search
CPC .............................. H03K 5/1504; G06F 1/10
USPC ................... 327/291–297; 716/114
See application file for complete search history.

(56) References Cited

U.S. PATENT DOCUMENTS

| | | |
|---|---|---|
| 5,331,966 A | 7/1994 | Bennett et al. |
| 5,365,182 A | 11/1994 | King |
| 5,506,520 A | 4/1996 | Frank et al. |
| 5,564,022 A | 10/1996 | Debnath et al. |
| 5,573,003 A | 11/1996 | Mann et al. |
| 5,818,263 A | 10/1998 | Ashuri |
| 5,923,188 A | 7/1999 | Kametani et al. |
| 5,974,245 A | 10/1999 | Li et al. |
| 6,020,774 A | 2/2000 | Chiu et al. |
| 6,148,432 A | 11/2000 | Brown |
| 6,198,978 B1 | 3/2001 | Takahashi |
| 6,216,256 B1 * | 4/2001 | Inoue ............... G06F 17/5031 326/101 |
| 6,378,123 B1 | 4/2002 | Dupenloup |
| 6,496,058 B1 | 12/2002 | Hong |
| 6,550,044 B1 * | 4/2003 | Pavisic ............. G06F 17/5045 716/114 |
| 6,667,645 B1 | 12/2003 | Fletcher et al. |
| 6,698,006 B1 | 2/2004 | Srinivasan et al. |
| 6,711,724 B2 * | 3/2004 | Yoshikawa ............ G06F 1/08 712/10 |
| 6,737,902 B2 * | 5/2004 | Tomsio ................. G06F 1/10 327/293 |

(Continued)

*Primary Examiner* — Thomas Skibinski

(57) ABSTRACT

An integrated circuit includes a clock tree network that distributes a clock signal to a plurality of clocked components of the integrated circuit. The clock tree network includes clock lines, each of which includes a clock tree delay element that provides a modified clock signal that is provided to an individual one the clocked components. Among the plurality of clocked components, one or more of the clocked components provides a data signal to another one or more of the clocked components. The one or more clocked components are configured having a transmission duration for the data signal that is longer relative to a transmission duration of the modified clock signal of the receiving clocked component.

22 Claims, 5 Drawing Sheets

(56) References Cited

U.S. PATENT DOCUMENTS

| | | |
|---|---|---|
| 6,769,104 B2 | 7/2004 | Rodgers et al. |
| 6,782,519 B2 | 8/2004 | Chang et al. |
| 6,810,508 B1 | 10/2004 | Bloom et al. |
| 6,819,150 B1 | 11/2004 | Santosa et al. |
| 6,941,533 B2 | 9/2005 | Andreev et al. |
| 6,943,610 B2 | 9/2005 | St-Laurent |
| 7,028,273 B2 | 4/2006 | Kanamaru et al. |
| 7,039,891 B2 | 5/2006 | Tetelbaum |
| 7,047,504 B2 | 5/2006 | Kawano |
| 7,117,472 B2 | 10/2006 | Auracher et al. |
| 7,178,124 B1 | 2/2007 | Makarov et al. |
| 7,207,024 B2 | 4/2007 | Scheffer |
| 7,219,320 B2 | 5/2007 | Kawano et al. |
| 7,325,211 B1 | 1/2008 | Bistry |
| 7,356,785 B2 | 4/2008 | Lu et al. |
| 7,526,666 B1 | 4/2009 | Soni |
| 7,546,560 B2 | 6/2009 | Dirks et al. |
| 7,562,316 B2 | 7/2009 | Tschanz et al. |
| 7,583,106 B2 | 9/2009 | Cumming et al. |
| 7,634,749 B1 | 12/2009 | Cortadella et al. |
| 7,643,591 B2 | 1/2010 | Arsovski et al. |
| 7,739,641 B1 | 6/2010 | Barnes |
| 7,810,061 B2 | 10/2010 | Minonne et al. |
| 7,996,804 B2 | 8/2011 | Nikitin et al. |
| 8,108,557 B2 | 1/2012 | Anderson |
| 8,205,182 B1 | 6/2012 | Zlatanovici et al. |
| 8,572,418 B2 | 10/2013 | Singasani |
| 8,593,177 B2 | 11/2013 | Iyer et al. |
| 8,839,178 B1 | 9/2014 | Walsh et al. |
| 2001/0052096 A1 | 12/2001 | Huijbregts |
| 2002/0087146 A1 | 7/2002 | Schu et al. |
| 2003/0182634 A1 | 9/2003 | Chang et al. |
| 2003/0189451 A1 | 10/2003 | Ziesler et al. |
| 2007/0063751 A1 | 3/2007 | Kanda et al. |
| 2011/0254588 A1 | 10/2011 | Nacer et al. |

\* cited by examiner

IMPLANTABLE MEDICAL DEVICE HAVING CLOCK TREE NETWORK WITH REDUCED POWER CONSUMPTION

FIELD

This disclosure relates generally to implantable medical devices, and more particularly to integrated circuits for reducing power consumption.

BACKGROUND

A wide variety of implantable medical devices (IMDs) that employ electronic circuitry for providing electrical stimulation of body tissue and/or monitoring a physiologic condition are known in the art. A number of IMDs of various types deliver electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and implantable cardioverter/defibrillators (ICDs) have been developed for maintaining a desired heart rate during episodes of bradycardia or for applying cardioversion or defibrillation therapies to the heart upon detection of malignant tachyarrhythmias. Other IMDs have been developed for applying electrical stimulation or other therapies, e.g., drugs, to nerves, the brain, muscle groups and other organs and body tissues for treating a variety of conditions.

The earliest IPGs employed very simple analog circuit oscillators formed by discrete transistors and other circuit components and were very short-lived and electrically inefficient. Integrated circuit (IC) technology and battery improvements were made that enabled hermetic sealing of IMD housings, improved reliability and lengthened the operating life of the IMD. Improvements to the early IPGs included incorporation of an analog IC with digital IC into an operating system architecture providing an array of sophisticated operating functions, programmability of operating modes and parameters, data storage, and uplink telemetry functions. Successive generations of IMDs of this type have incorporated increased operating modes and functions through further improvements in circuitry and long-lived, low current output, low voltage batteries. Most recently, a wide number of IMD system architectures have been developed that incorporate custom microcomputers comprising a microprocessor, RAM and ROM, bus, and related elements of a typical microcomputer and other control logic, memory, input signal processing circuitry and therapy delivery output circuitry. The complexity of the circuitry, the functions provided, the longevity, and the reliability of the IMDs have all increased dramatically while the IMD size has decreased.

Current IMD operating system architectures typically are embodied in one or more IC(s) and discrete components mounted to one (or more) substrate employing hybrid fabrication circuitry techniques. The ICs may include one or more circuit blocks, each of which includes a plurality of circuitry components. Certain of the circuitry components on a particular IC perform analog or digital functions, input signal processing, and output therapy delivery. Digital logic ICs or circuitry are formed employing complementary metal oxide semiconductor (CMOS) fabrication technology. The digital logic ICs perform signal processing, timing, and state change functions embodying Boolean logic timed synchronously by a system-wide clock.

Even with these improvements, such digital logic ICs including those assembled from various clocked components such as logic gates, flip-flops, latches, and other Boolean logic blocks used in IMD system architectures suffer from several limitations and disadvantages. It is necessary to route clock distribution over the complete IC chip area as a clock tree of discrete electrical conductors or lines to reach all clocked components. The clock tree takes up IC chip real estate that could be used to increase device functions or memory capacity, dissipates power as heat, and increases overall power drain of the IC, decreasing useful life of the IMD battery. The clock tree also requires complex timing analysis and worst case design analysis and simulation to ensure design integrity because of possible clock skew and the resultant timing errors induced by race conditions. It would be desirable to minimize the use of IC real estate occupied by the clock tree, to simplify design analysis and simulation of the IMD system architecture and to decrease power consumption while increasing and improving processing capabilities of such IMDs.

SUMMARY

In general, the disclosure pertains to techniques for optimizing power consumption of low power devices having clocked integrated circuits. The integrated circuits for which the present disclosure is contemplated have a global clock tree network having clock lines through which clock signals generated by a clock are provided to clocked components that are coupled to the clock lines.

To achieve the optimization, techniques are described for reducing the complexity of the global clock tree network design as a function of the clocked components coupled to the clock lines of the clock tree network. Among other things, the reduction in complexity involves a reduction in the size and number of clock tree delay elements placed along clock lines of the global clock tree network.

In accordance with an embodiment, an integrated circuit includes a clock tree network that includes multiple clock lines that distribute a clock signal to a plurality of clocked components of the integrated circuit. The clocked components may include a plurality of flip-flops or latches each of which is connected to one of the clock lines. In some implementations, data may be provided from a first (transmitting) of the clocked components to a second (receiving) of the clocked components in the integrated circuit through a first data signal line coupling a data output of the first clocked component to a data input of the second clocked component. A transmission path of the data signal within the first clocked component is configured based on the clock line of the second clocked component to effect the propagation of the data signal from the first clocked component to the second clocked component subsequent to receipt of the clock signal by the second clocked component.

In an embodiment, the clock line of the second clocked component includes a clock tree delay element that receives the clock signal and generates a modified clock signal. The first clocked component is configured with a data signal transmission path for transmission of data from the first clocked component to the second clocked component subsequent to the receipt, by the second clocked component, of the modified clock signal.

The foregoing has outlined rather broadly certain features and/or technical advantages in order that the detailed description that follows may be better understood. Additional features and/or advantages will be described hereinafter which form the subject of the claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The present disclosure can be practiced in the context of the systems described herein. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are many discrete processes involving collecting, storing, and presenting physiologic trends of a patient, as well as in delivering therapies (e.g., a cardiac therapy). The battery located within an implantable medical device (IMD) provides the power necessary for performing such operations. Therefore, conserving battery power can provide for longer, uninterrupted operation of the IMD. Many techniques have been utilized in order to conserve power. The present disclosure proposes such techniques that are associated with reduction of power consumption for conservation of the battery power.

Figure 1:
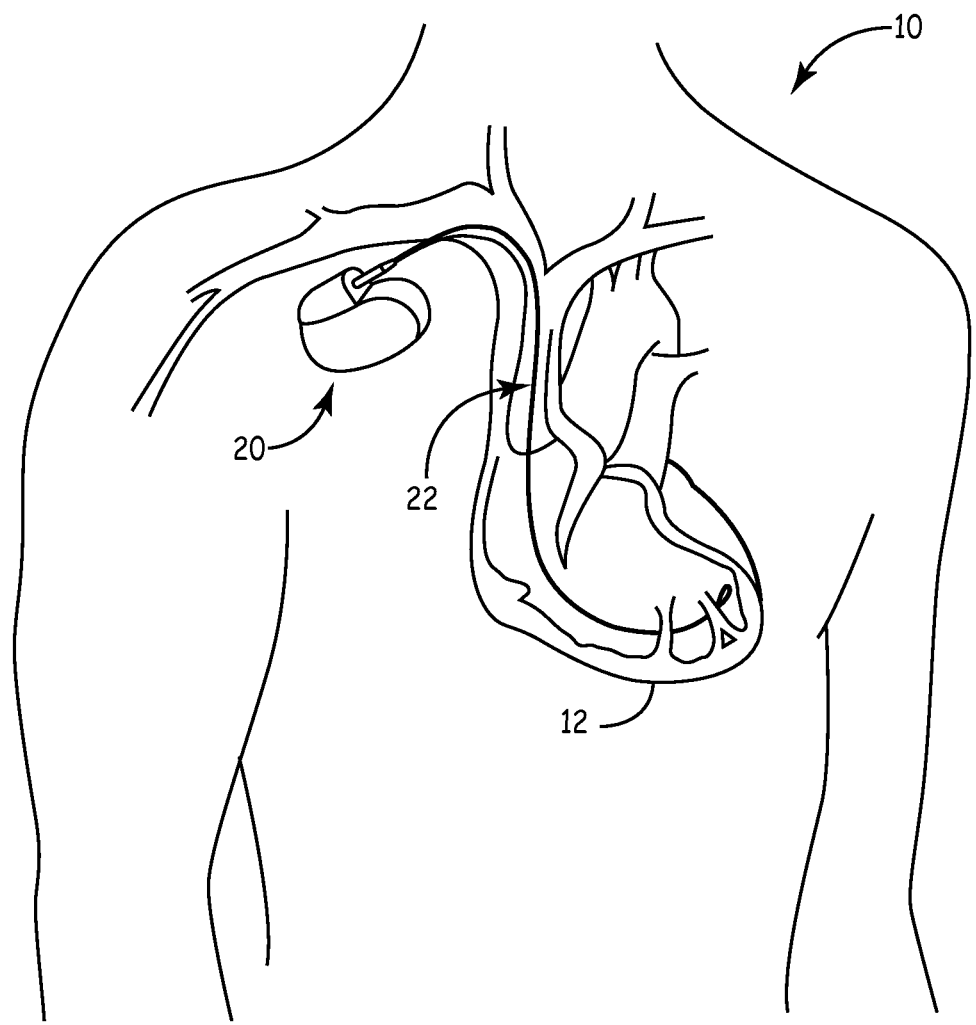
FIG. 1 illustrates an implantable system in accordance with one exemplary embodiment of the disclosure.

FIG. 1 illustrates an implantable system in accordance with one exemplary embodiment of the disclosure. An IMD 20 is implanted in a body 10 near a heart 12. IMD 20 includes circuitry, a battery and other components that are contained within a hermetically sealed, biologically inert outer canister or housing that may be conductive so as to serve as a pace/sense electrode in the pacing/sensing circuit. One or more leads, herein, collectively identified with reference numeral 22, electrically couple to the IMD 20 and extend into the heart 12. In the case where IMD 20 is a pacemaker, leads 22 are pacing and sensing leads to sense electrical signals attendant to the depolarization and repolarization of the heart 12 and provide pacing pulses in the vicinity of the distal ends thereof. One or more exposed conductive pace/sense electrode(s) for sensing electrical cardiac signals or delivering electrical pacing pulses to the heart 12 are disposed at or near the distal ends of the leads 22. The leads 22 may be implanted with their distal ends situated in the atrium and/or ventricles of the heart 12 or elsewhere in cardiac blood vessels in operative relation with a heart chamber. The leads 22 can also carry other sensors for sensing cardiac physiologic data, e.g. pressure, temperature, impedance, pH, blood gas, acceleration, etc.

IMD 20 may also be a pacemaker/cardioverter/defibrillator (PCD) corresponding to any of the various commercially-available implantable PCDs. Those and other alternative implantable devices may be employed using the present disclosure in that such devices may employ or be modified with circuitry and/or systems according to the present disclosure. Examples of such alternative devices of IMD 20 may be an implantable nerve stimulator or muscle stimulator. In fact, the present disclosure is believed to find wide application in any form of electrical device which uses CMOS, SOS, SOI, BICMOS, PMOS, and/or NMOS based integrated circuits, and is further believed to be particularly advantageous where low power consumption is desired, particularly in battery powered devices.

In general, IMD 20 includes a hermetically-sealed enclosure that includes a power source and circuitry to control therapy delivery to heart 12. The circuitry may be implemented in discrete logic and/or may include a microcomputer-based system with A/D conversion.

For a time, early, large scale and relatively primitive, integrated circuits (ICs) did not rely upon clocked components or CMOS circuitry, and instead operated asynchronously. However, clocked computer system architectures replaced the early asynchronous architectures, and computer clock speeds have steadily increased. Increasing the speed at which a digital logic device transitions between logic states, commonly referred to as switching speed, has long been a primary motivation behind many of the advancements in the semiconductor arts to increase computing and signal processing power. Today, the construction of ICs for implantable medical devices has utilized CMOS technology advancements that are below sub-micron levels, such as the 250 nm and 90 nm CMOS process technologies. The ICs include one or more circuit blocks, each having a plurality of electronic components. The factors that were of primary significance in achieving these advanced processing technologies to the circuit block included speed and area.

However, the combined effect of having large die surface area and many gated clocks to reduce the dynamic circuit power is making it difficult to distribute a clock signal uniformly throughout the circuit block with minimal clock skew, and low power. Generally speaking, the inventors of the present disclosure have observed that up to approximately thirty (30) percent of the power consumption in current digital designs is associated with the distribution of a clock signal to all flip flops of the IC. This estimate has especially been observed for full scan designs of the circuitry of an implantable medical device (IMD) such as those manufactured by the assignee of the present disclosure.

Figure 2:
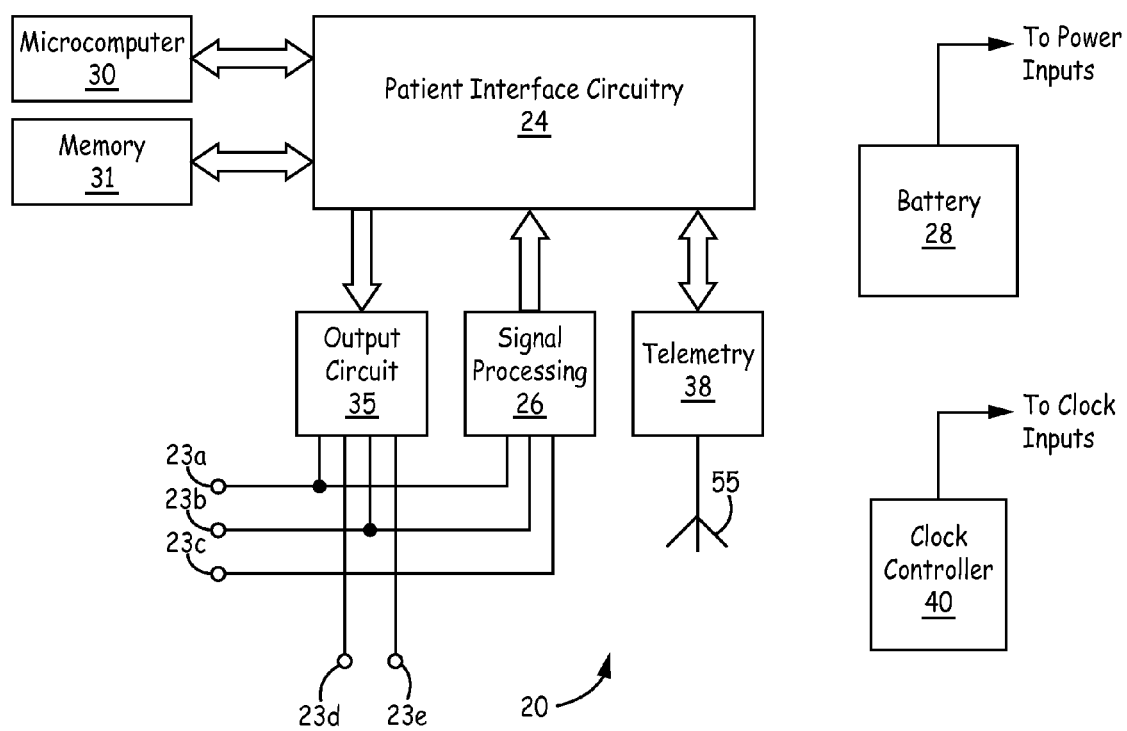
FIG. 2 depicts an embodiment of an implantable medical system architecture.

Referring now to FIG. 2, an embodiment of an implantable medical system architecture is illustrated. The system may include IMD 20 implanted into the patient's body 10, which is an example of the type of devices in which the present disclosure can be implemented. The IMD 20 provides delivery of a therapy and/or physiologic input signal processing in which clocked integrated circuits are selectively incorporated in accordance with the present disclosure. However, the discussed aspects of the IMD 20 could be implemented in a wide variety of devices, including pacemakers, defibrillators, etc.

The components of the IMD 20 illustrated in FIG. 2 are microcomputer-based control and timing system 30, memory 31, patient interface circuitry 24, a telemetry/programming unit 38, and a clock source 40. Although not illustrated in the figure, various components of the IMD 20 are communicatively coupled to each other for transfer of data between the components. Examples of coupling techniques for communication between the components include a communication bus or a conductive pathway and the data that is transferred from one circuit or component to another circuit is propagated through such coupling medium.

The microcomputer 30 varies in sophistication and complexity depending upon the type and functional features incorporated therein. The functions of the microcomputer 30 are controlled by firmware and programmed software algorithms stored in FLASH, RAM and ROM including PROM and EEPROM and are carried out using a CPU, ALU, etc., of a typical microprocessor core architecture. The microcomputer 30 may also include a watchdog circuit, a DMA controller, a block mover/reader, a CRC calculator, and other specific logic circuitry coupled together by on-chip data bus, address bus, power, clock, and control signal lines in paths or trees.

Memory 31 can include read only memory, typically used to store the basic programming for the IMD 20, including the primary instructions set defining the computations performed to derive the various timing intervals performed by IMD 20. Memory 31 can also include random access memory, typically used to store the values of variable control parameters, such as programmed pacing rate, pulse widths, pulse amplitudes, and so forth, which are programmed into IMD 20 by the physician.

The IMD 20 typically includes patient interface circuitry 24 for receiving signals from sensors or electrodes located at specific sites of a patient's body 10 and/or delivering a therapy to a site of the patient's body. The typical patient interface circuitry 24 comprises a therapy delivery system 35 and/or a physiologic input signal processing circuit 26 or simply one or the other. Output circuit 35 is controlled by microcomputer 30 to determine the amplitude and pulse width of the pulse to be delivered and to determine which electrode(s) is to be employed to deliver the pulse.

The therapy delivery system 35 can take a variety of forms and typically involve delivering electrical stimulation to body muscle groups, the heart, the brain, other organs, selected nerves, and the spinal column or the delivery of drugs into organs for therapeutic treatment or into the spinal column for pain relief. It will be understood that most of these therapy delivery IMDs also have a physiologic input signal processing circuit 26 that processes physiologic signals that are used to trigger or modulate therapy delivery and are stored as physiologic signal data for later retrieval as described above. The therapy delivery system 35 may be configured to include a substance delivery apparatus or pump which is coupled to a suitable catheter extending to a site of the patient's body to deliver a substance, e.g., a therapeutic or diagnostic agent or drug, from a substance reservoir.

The output circuit 35 is coupled to electrodes 23*a* and 23*b* which are employed both for delivery of pulses and for sensing of cardiac signals. Electrode 23*a* may be located on the distal tip end of a lead and is preferably placed in the apex of the right ventricle for ventricular pacing; for atrial pacing, it is placed in the patient's atrium. Electrode 23*b* may be a ring electrode, as used with a bipolar lead. Electrode 23*c* represents the device housing, which may be used as the indifferent electrode for selected unipolar pacing and/or sensing operations. For a dual or multi-chamber pacing system, additional electrodes are employed. For example, electrodes 23*d* and 23*e* may be used for pacing and sensing in the atrium, while electrodes 23*a* and 23*b* are used in the ventricle.

The physiologic input signal processing circuit 26 is coupled to electrodes and/or physiologic sensors on or in the housing of the IMD 20 or situated at sites distanced from the IMD housing, typically on electrodes of the lead 22 (FIG. 1) for sensing of cardiac signals. For example, bipolar and/or unipolar sensing may be used. In one embodiment, a unipolar lead in the atrium and a unipolar lead in the ventricle are used, e.g., the signals are picked up at electrodes 23*a* and 23*d*. Sense signals are input into signal processing circuit 26—or other DSP circuit, which comprises a number of signal processing channels corresponding to signals of interest. For example, in a dual chamber pacemaker that incorporates P wave processing either for rate control, capture detection or any other reason, there would preferably be three channels for respective signal processing of the P, R and T waves. The data resulting from the signal processing is utilized by the microcomputer 30 for the signal classification operations, as well as any other necessary calculations.

External control of the implanted device is accomplished via telemetry/control block 38, which allows communication between the implanted device and an external programmer via antenna 55. The IMD 20 may also comprise an implantable cardiac monitor without a therapy delivery system 35, e.g., an implantable EGM monitor for recording the cardiac electrogram from electrodes remote from the heart as disclosed in commonly assigned U.S. Pat. No. 5,331,966. In these monitor embodiments, physiologic data, e.g., the cardiac EGM and/or sensor derived data is typically stored in RAM in microcomputer-based control and timing system 30 for uplink telemetry to the external programmer when the IMD 20 receives a downlink telemetered interrogation command from the programmer.

All current IMDs rely upon a source of electrical energy to power the IMD operating system including the circuitry of IMD 20 and to power any electromechanical devices, e.g., valves, pumps, etc. of a substance delivery IMD or to provide electrical stimulation energy of an ICD shock generator, cardiac pacing pulse generator or other electrical stimulation generator. The typical energy source is a high energy density, low voltage battery 28. The energy source 28 provides one or more low voltage power, one or more VREF power, current sources, and, in the case of an ICD, high voltage power to the therapy delivery system 35.

The IMD 20 may be fabricated as described employing circuit blocks having clocked components that require a clock signal provided by a clock 40 coupled thereto. In FIG. 2, each clock signal generated by clock 40 is routed to all applicable clocked components via a clock tree network (not shown). The clock 40 provides one or more fixed frequency clock signal(s) that, in some embodiments, may be independent of the battery voltage over an operating battery voltage range for system timing and control functions. In some embodiments, additional clock sources may be provided in some embodiments to clock multiple segments of the circuit blocks independently. The clock signal(s) output by the clock 40 represents at least one and possibly a plurality of differing frequency clock signals that are employed in certain instances in the therapy delivery system 35, in clocked timers of the microcomputer-based control and timing system 30, and in formatting uplink telemetry signal transmissions in the telemetry circuit 38. In accordance with some embodiments, the clock(s) 40 may be gated to be active periodically as needed by one or more circuit blocks. All logic gates of the clocked components are preferably switched in state within one clock cycle. Self-timed logic and other un-clocked components may be employed in other parts of therapy delivery system 35, the microcomputer-based control and timing system 30, and in certain downlink telemetry signal reception and decoding stages in the telemetry circuit 38.

In accordance with the present disclosure, the clock signal is distributed to various clocked components in one or more circuit blocks of the IMD 20 via improved clock tree networks and improved clocked component design and selection criteria. The improved clocked components may include flip-flops, latches, and other integrated circuit elements including those that change state in response to a clock signal pulse. The state changes may be synchronized in a group of the clocked components by clocking the components with the same clock signal.

Figure 3:
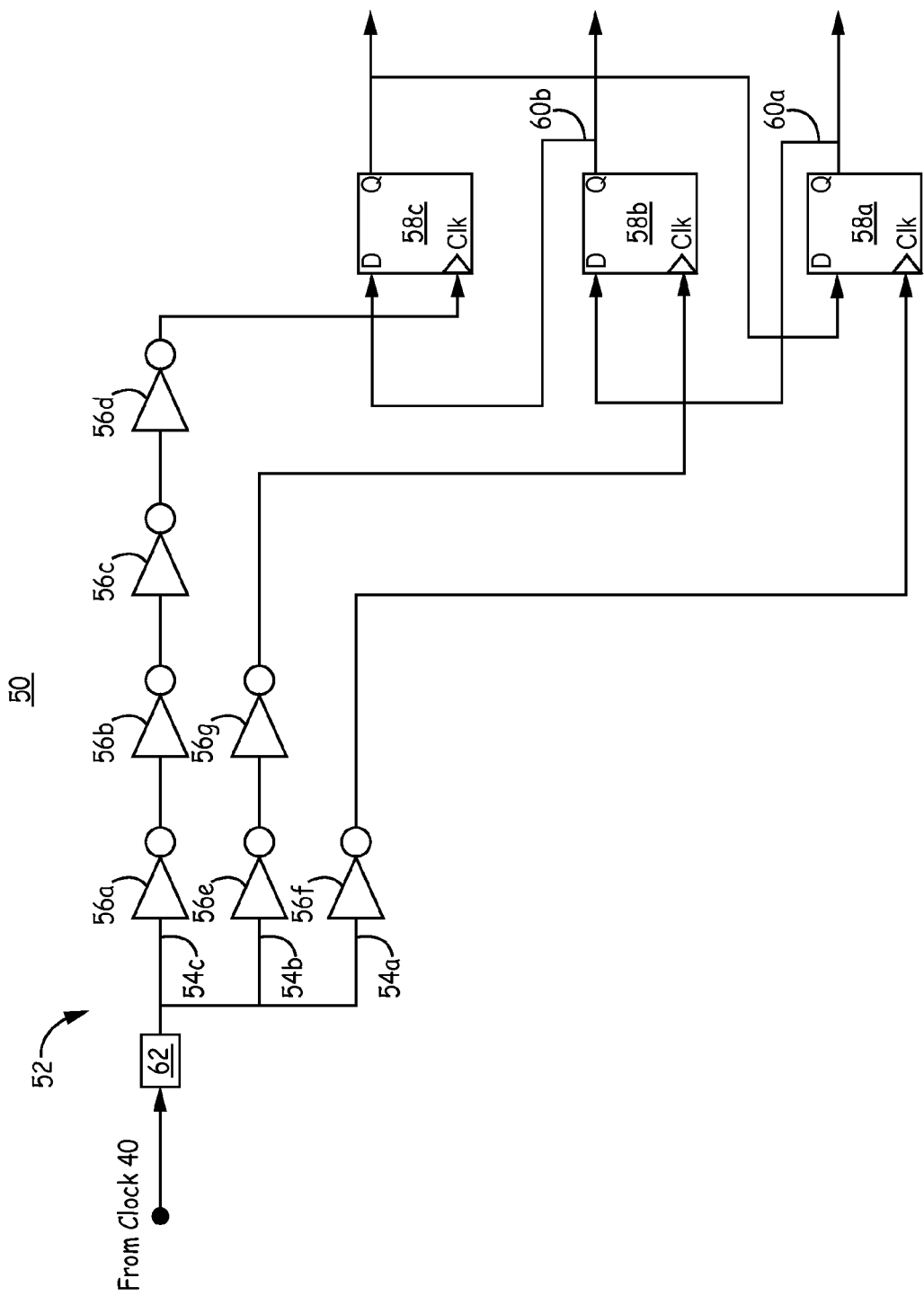
FIG. 3 illustrates a portion of an integrated circuit having a clock tree network for distribution of a clock signal in accordance with an embodiment of the disclosure.

FIG. 3 illustrates a portion of a circuit block having a clock tree network for distribution of a clock signal in accordance with an embodiment of the disclosure. Like members are designated by like reference characters. The circuit block 50 includes a clock tree 52 that is comprised of a plurality of clock lines 54a, 54b, 54c (collectively "54"). Each of the clock lines 54 includes one or more clock tree delay element(s) 56a-g (collectively "clock tree delay element(s) 56") and with each of the clock lines being connected to a clock source, such as clock 40 (FIG. 2) at an input terminal 62 located at a first end of the clock tree 52. The clock tree delay elements may comprise one or more buffers and/or inverters. The circuit block 50 further includes a plurality of clocked components 58a-c, such as flip-flops, (collectively "clocked components 58").

The clock source 40 may be on-chip or off-chip with the circuit components of circuit block 50. The clock source 40 may be coupled to one or more of the clocked components through the clock tree 52. For example, the second ends of the clock lines 54 may be individually coupled to one of the plurality of clocked components 58. The clock lines 54 may include gating elements to enable or disable portions of the clock tree to lower dynamic power consumption.

The clocked components of an exemplary IMD 20 to which the clock signal is distributed will typically be located throughout the circuit block 50. Since the clock signal must travel through different distances to get to the different clocked components, the clock signals often become skewed relative to each other. Specifically, each clock signal is distributed across the clock tree 52 and provided to each clocked component through the clock lines 54 for timing information. In the example of the clocked components 58 being implemented as flip-flops, the clock signal causes the flip-flops to either change or retain its output signal based upon the values of the input signals at the transition of the clock signal. Within the circuit block 50, data may be shared among the one or more clocked components. For example, the plurality of clocked components 58 may be interconnected at defined data input and output lines, as will be described below, to share data.

A data line 60a may couple the output of clocked component 58a to the input of clocked component 58b. Another data line 60b may couple the output of clocked component 58b to the input of clocked component 58c. Each of the data lines 60 carries information generated at the output of the clocked component output terminal to the coupled clocked component input terminal. If a data signal from one clocked component, driven using a first clock line is sent to a different clocked component that is clocked using a second clock line, timing issues may arise. Specifically, if the clock tree including the two clock lines does not meet certain criteria then the data signal will not be captured in the correct clock cycle or will not be captured reliably. For example, if the clock line to clocked component 58b is slower than the clock line to clocked component 58a, then the data signal from clocked component 58a may be generated, transmitted to and sampled by clocked component 58b at an incorrect time, i.e., before the clock signal is received. This situation is referred to as a "race condition." Race conditions can cause inaccurate processing because the data value is read when a data signal is sampled with inaccurate timing. Thus race conditions can cause circuit block 50 to not function properly.

In an attempt to resolve the race conditions, one conventional approach has been to modify the number of clock tree delay elements 56 coupled to the clock line 54. The modification of the number of clock tree delay elements 56 is performed to meet the requirement that the clock signal must arrive at each clocked component a predefined time. Accordingly, digital design tools have been developed that evaluate the timing along each of the clock lines 54 during the design of the circuit block 50 to determine clock lines that have mismatched timing with regards to the arrival of the clock signal at the plurality of clocked components 58. The tools remedy the mismatch by adding or subtracting clock tree delay elements 56 to slow down the signal in the fast clock lines 54 and speed up slow clock lines 54. As a result of this complex evaluation, the number and size of clock tree delay elements 56 in the entire clock tree network 52 is increased. The increase in the number and size of clock tree delay elements 56 correspondingly increases the size of the clock tree 52 and hence the size of the circuit block 50. Owing to the clock tree size (in terms of number and size of components) the inventors have observed in at least some designs current consumption in excess of about 30% of the total IMD digital current budget. Reducing the current consumption of the clock tree is desirable because it facilitates longevity of the IMD operation.

The inventors of the present disclosure have observed that utilizing modern processing technology advancements that are below sub-micron levels, such as the 250 nm or smaller CMOS process technologies, the operating frequency of many of the clocked components of low power devices can significantly be reduced to achieve a reduction in the clock tree consumption. In such sub-micron process technologies, the design of the device circuitry for most low power devices including implantable medical devices is not speed constrained. In such devices, the clocked components can be designed to satisfy the timing requirements for the slowest path for propagation of data from one clocked component to another interconnected clocked component without impacting the circuit's functionality.

Figure 4:
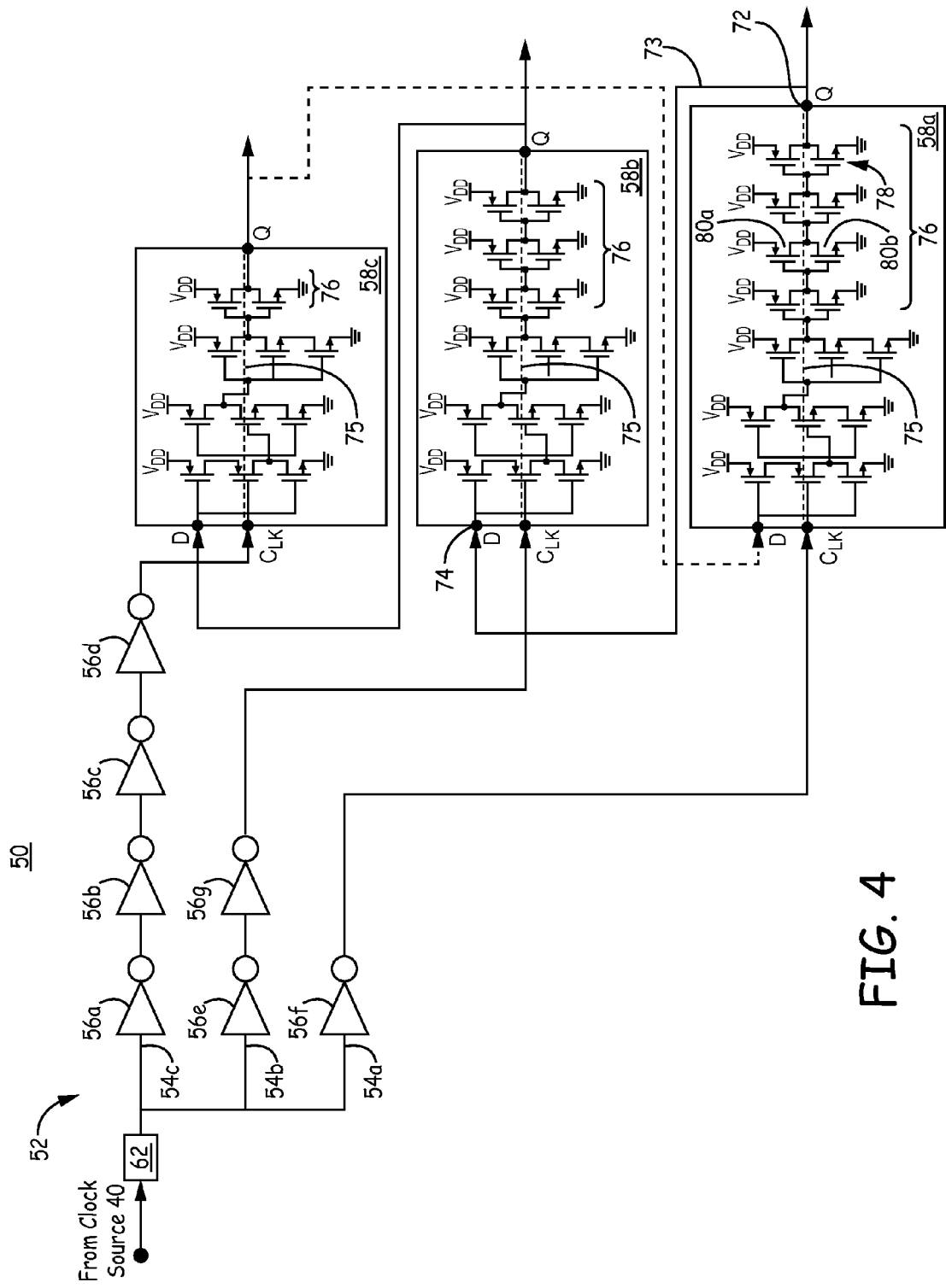
FIG. 4 illustrates a schematic view of an integrated circuit including a clock tree network and a plurality of flip-flops according to an embodiment of the disclosure.

FIG. 4 illustrates a schematic view of the circuit block 50 including a clock tree network and a plurality of clocked components according to an embodiment of the disclosure.

The exemplary schematic described in FIG. 4 is implemented in accordance with a solution proposed by the inventors for eliminating race conditions. Circuit block 50 includes clock tree network 52 and clocked component 58.

There are a variety of types of flip-flops and the D flip-flop illustrated in FIG. 4 is but one example of such flip-flops. The illustration of the flip-flop is merely for ease of discussion and the disclosure is not intended to be limited to that type of clocked component. Rather, those skilled in the art will appreciate that the disclosure is equally applicable to other clock-controlled components having a data input and a data output. The clock signal is provided to the circuit block 50 at an input terminal 62 of the circuit block 50. That clock signal is distributed, via the clock tree 52, to all clocked components of the circuit block 50. In the illustrative embodiment, the clocked component 58 captures the data value at a predefined edge of the clock. For example, the clocked component 58 may capture the data on the rising or falling edge of the clock signal. That captured data value becomes the Q output. In order for the circuit block 50 to function correctly, e.g., without a race condition, the clock signal must arrive to each clocked component at approximately the same time and the data inputs to the clocked component 58 must not change just prior to, or just after the clock edge.

In many IMD circuit designs, some of the clocked components 58 are designed to provide data to other clocked components within the circuit block 50. That is, the input data value that is captured by a receiving clocked component 58b may be received from a transmitting clocked component 58a. Therefore, a clock signal distributed to such clocked components needs to be timed such that the data that is provided by the transmitting clocked component 58a on a clock edge does not arrive at the input terminal of the receiving clocked component 58b prior to the clock signal corresponding to the same clock edge arriving at the receiving clocked component 58b. Otherwise, if the transmitting clocked component 58a generates and propagates the data from input to output at a speed that causes the data to arrive at the receiving clocked component 58b prior to arrival of the clock signal, clocked component 58b captures the incorrect data.

In such scenarios, the present disclosure facilitates the design of a circuit in which the transmitting clocked component 58a ensures that a data value is provided as input to the receiving clocked component 58b with the appropriate timing. By way of non-limited example, the present disclosure describes a design in which the propagation speed of the data within transmitting clocked component 58a is reduced. The reduction in speed within the transmitting clocked component 58a is achieved by adding clocked component delay elements and/or resizing the clocked component delay elements in the transmission (clock-to-Q) path 75 of the transmitting clocked component 58a. In one example implementation, the inventors slowed down the transmission path 75 of a clocked component (flip-flop) from a speed of 4.5 nanoseconds (ns) to a speed of about 8 ns. The reduction of propagation speed in transmitting clocked component 58a prevents race conditions and lowers power in the clock tree. An additional benefit is that the overall number of clock tree delay elements 56 that are coupled to the clock lines 54 can be reduced resulting in, one example, a savings of approximately 30 microamperes (uA) of clock tree power. The reduction in the overall number of clock tree delay elements 56 also facilitates a decrease in the overall size of the circuit block 50, which facilitates miniaturization of the device. Alternatively, the unused space may be occupied by other circuit elements to increase the functionality of circuit block 50. Moreover, the present disclosure increases the tolerance of a circuit design to variations in the process, temperature, and voltage conditions which is facilitated by the relative independence of routing parasitics, partly as a result of the enhanced control of the internal delay of the plurality of clocked components 58.

While not intended to be limiting, a discussion of the transmission of a data signal from one clocked component to another clocked component is provided with a specific implementation comprising flip-flops. It should be understood that the reference to flip-flop components is simply for ease of illustration, it being understood that the principles are similarly applicable to other clocked components. As such, in one embodiment, the present disclosure provides the circuit block 50 having flip-flop 58a and flip-flop 58b that are coupled to clock source 40 through clock line 54a and clock line 54b, respectively. The clock lines 54a, 54b (collectively "clock line(s) 54") may be of differing lengths depending on the location of the flip-flops 58. As such, the same clock signal propagated along the clock tree 52 will arrive at differing times to the respective flip-flops 58. In other embodiments, the clock lines 54 may include unequal numbers of clock tree delay elements 56 that are coupled to the clock lines 54 to receive a clock signal transmitted to the flip-flops 58a and 58b. The clock tree delay element 56 functions to slow down the propagation of the clock signal; as such the clock signal received by the clock tree delay element 56 is output as a modified clock signal.

A data output terminal 72 (Q) of flip-flop 58a is coupled to a data input terminal 74 of flip-flop 58b. The data output terminal 72 is coupled through a data line 73 to the data input terminal 74. As is further illustrated, the internal structure of the flip-flops 58 includes a transmission line or transmission path 75 for the data signal that is transmitted to the output terminal 72.

In accordance with an embodiment of the present disclosure, a first or subsequent transmitter flip-flop 58a is selected from a library of flip-flops such that the flip-flop 58a satisfies a criteria that the combined durations of propagation of the clock signal along clock line 54a and the propagation of the data signal within the flip-flop 58a is greater than the duration of propagation of the clock signal through clock line 54b. In other words, the flip-flop 58a will have a transmission path 75 ($C_{LK}$-to-Q) for propagation of data through the flip-flop 58a with a duration that causes the data to be received by the flop-flop 58b subsequent to (or, a point in time after) receipt of the modified clock signal. The library of flip-flops will have a plurality of flip-flops, each having transmission paths 75 that provide varying transmission speeds, and therefore, the criteria enables selection of an appropriate flip-flop from the library. The criteria thus effects a reduction in the transmission speed (and increased transmission duration) of the data which enables a reduction in the size of the clock tree 52.

In yet other embodiments, the criteria for selecting one of the flip-flops from a library of flip-flops may alternatively be based on the transmission delay of the data line 73 interconnecting the data output terminal of flip-flop 58a and the data input terminal of flip-flop 58b. Such an implementation may be especially suitable for a circuit design that is not speed constrained. An example of such a circuit is the circuit of a low power device that is fabricated with sub-micron process technologies. In such embodiments, the pair of flip-flops 58 having the longest transmission duration of a data signal from data output terminal 72 to the data input terminal 74, coupled through data line 73 is identified. In the embodiment, the flip-flop 58a may be selected based on the duration of the data line 73 to satisfy the condition that the combined duration of the transmission path 75 delay and the data line 73 delay is greater than the propagation of the clock signal to the flip-flop 58b.

The transmission path 75 of the data within the flip-flop 58a includes one or more clocked component delay elements 76a-76d (collectively "clocked component delay element(s) 76") that are provided to control the duration of propagation of the data signal. Examples of the clocked component delay element may include one or more buffers and/or inverters. As such, the flip-flops in the library of flip-flops will have differing numbers and/or sizes of clocked component delay elements 76 to provide a plurality of differing predetermined durations of propagation of a data signal within any given flip-flop's transmission path. In other words, the present disclosure provides for selection of one of the plurality of flip-flops in the library that provides a transmission path 75 having a duration that facilitates the modified clock signal to be received by the flip-flop 58b prior to the data signal being output at terminal 72.

In accordance with an embodiment of the disclosure, selection of the given flip-flop 58a may be based on the duration for propagation of the data signal within flip-flop 58a, which is a function of the capacity of the clocked component delay elements 76 that are coupled to the transmission path 75. As one illustration of varying the capacity, clocked component delay elements 76 may comprise a buffer, or multiple inverters 78, each of which is comprised of at least two transistors 80a, 80b, or one or more transistor(s) connected as load elements (not shown). The capacity of the clocked component delay elements 76 may be increased by increasing the number of discrete components comprising the clocked component delay elements 76 that are coupled to the transmission path 75 or by increasing the buffer stages. Another example may involve changing the sizes of the individual components comprising the clocked component delay elements 76. As such, the increase in the capacity of the clocked component delay elements 76 will result in an increase in the duration of propagation of a data signal within the flip-flop 58a.

In accordance with an alternate embodiment, the selection will involve a comparison of the propagation delay of the data signal within flip-flop 58a by comparing flip-flops having clocked component delay elements 76 of differing sizes or number of elements. For example, for the implementation of the clocked component delay elements as transistors 80a, 80b, differing delays may be obtained by selecting flip-flops with transistors 80a, 80b with different widths and/or lengths. The goal of determining the clocked component delay element size is to provide a desired propagation delay of the data signal within flip-flops 58a, with the flip-flop 58a being selected from the library to meet the criteria discussed in this disclosure.

It should be noted that the description of the circuit block 50 in the context of slowing down the transmission path of flip-flop 58a is provided as a non-limiting example based on the data from flip-flop 58a being provided to flip-flop 58b with both flip-flops 58a and 58b receiving the same clock signal. It is contemplated that the same principles may be applied to effectively slow down the transmission path of flip-flop 58b in situations where flip-flop 58b provides data to flip-flop 58c with all three flip-flops receiving the same clock signal, and so forth for implementations with many more flip-flops and data paths.

In yet another embodiment, transmission path of the plurality of flip-flops 58 may be designed to meet a minimum requirement. As discussed elsewhere, the design of the IMD 20 circuitry is not speed constrained in the sub-micron process technologies in conventional use. Therefore, the worst case delay will generally satisfy the device functionality and the IMD 20 operation is not affected by operating the plurality of flip-flops 58 under the worst case delay conditions. For example, for an IMD 20 that is to be operated with an upper limit speed of 10 MHz (100 nS cycle) and that is deemed to have the slowest path delay of 60 nS for propagation of a data signal from the output terminal of first flip-flop 58a, and further, through other combinational logic (not shown in FIG. 4), for example, to the input of second flip-flop 58b, then the plurality of flip-flops 58 may be selected having a transmission path propagation delay of about 20 nS with the clock tree imbalance being as loose as 20 nS and the design would still perform as expected. Typical IMD clock rates are much lower than 10 MHz and in the smaller process nodes, such as those of the 90 nm processing technologies, generating a worst case path delay of 60 nS is very easy to do. In this example it would be possible to develop a clock tree network that could be as simple as 1 or 2 levels and still satisfy the timing requirements for a properly timed clock tree.

The foregoing figures have described exemplary ICs having clock trees coupling a clock signal to two or more clocked components included in a circuit block of the ICs. The two or more clocked components in the circuit block 50 that are to be driven by the same gated clock signal may be grouped into the same group. For example, the clocked components 58a, 58b, 58c that are to be driven by a first gated clock signal may be grouped into a first group. Those clocked components driven by a second gated clock signal may be grouped into a second group, and so forth. Further, those clocked components that are driven continuously without interruption by the system clock signal may be grouped into another group. The clock tree network distributing the clock signals to the groups of clocked components may be synthesized by a design tool to optimize the size of the clock tree network. Such tools are commonly referred to as clock tree synthesis (CTS) tools. Conventional CTS tools typically insert clock tree delay elements in selected clock lines of the clock tree to adjust the path delays within those clock lines to ensure that the clock tree will deliver each clock signal pulse to every clocked component within the group with as nearly as possible the same delay. Moreover, in situations in which one or more of the clocked components (transmitter) provides a data signal to another clocked component (receiver) as input to be processed based on a clock edge of the clock signal, the clock signal propagated to the receiving clocked component must be received prior to arrival of the data so that the receiving clocked component captures the data transmitted from the transmitting clocked component during the correct clock cycle. As such, the CTS tools will typically insert more clock tree delay element(s) in the clock line of the transmitting clocked component or data path delay element(s) along the data path coupling the transmitting clocked component and the receiving component. In either scenario, the insertion of the clock tree or data path delay element(s) is performed to delay the processing of the data signal and facilitate meeting the condition that the clock signal must arrive at the receiving clocked component prior to the data signal propagated from the transmitting clocked component. Examples of the CTS tool sets available for facilitating design testing of an circuit block 50 include software tools that are commercially available from Synopsys, Inc. and Cadence Design Systems, Inc., both of California.

However, as noted above, the process of optimizing the clock tree networks by inserting more clock tree delay elements increases the size and complexity of the clock tree while increasing current consumption and generally creating an inefficient integrated circuit.

Figure 5:
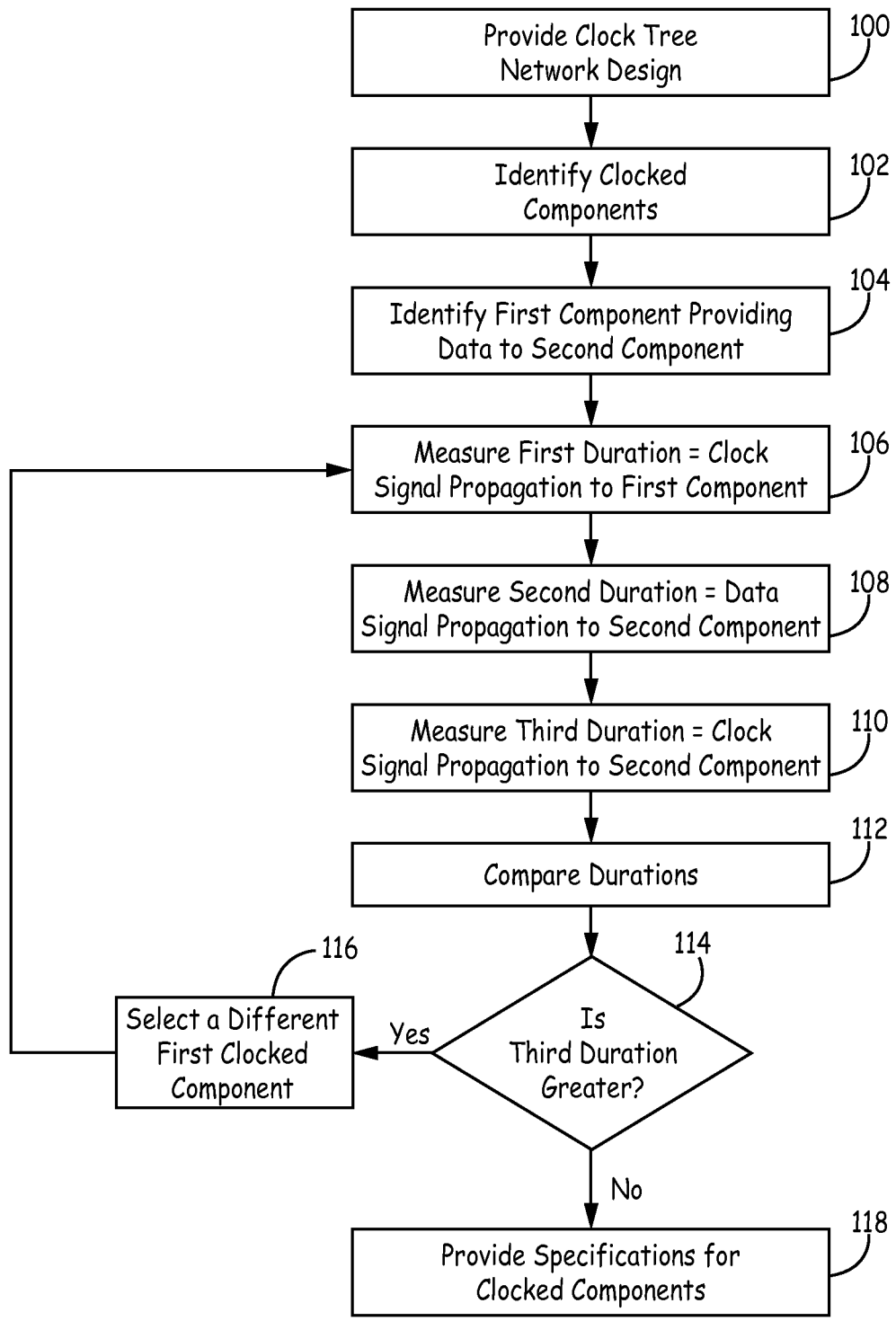
FIG. 5 illustrates a method in accordance with an embodiment of the disclosure for generating one or more low power clock trees included within an integrated circuit.

Referring to FIG. 5, a method is illustrated in accordance with an embodiment of the disclosure for generating one or more clock tree networks included within an integrated circuit. Various approaches to IC design include many tasks that culminate in generating an IC netlist. The netlist contains information on the circuit components, their interconnections, area used, and other details. The circuit designer may specify the constraints that are to be applied to ensure that the IC design meets the required functionality, specifications, and speed. It is typical to utilize a tool to verify the netlist for the requirements prior to performing the physical design. The techniques relating to the method of FIG. 5 may be employed by a CTS tool for synthesizing an IC in a manner that maintains predetermined criteria. The method may suitably be incorporated into software stored on computer readable media which, when read and executed by a computer, causes the computer to act as a CTS tool. Suitable computer-readable media for storing the instructions include, but are not limited to, compact disks, floppy disks, hard disks, and random access or read only memory.

In accordance with embodiments of this disclosure, the verification of the netlist may be performed by a CTS tool in conjunction with adjustments to the design of the clock tree network of an IC circuit block. The circuit block includes at least one group of clocked components that are to be driven by the same gated clock signal. The clocked components may include flip-flops, latches, and other clocked integrated circuit elements. Such a group of clocked components receive the clock signal through a clock tree network that includes a plurality of clock lines each defining a separate timing path. The CTS tool evaluates the timing paths to optimize the size and performance of the clock tree for optimal current consumption and accuracy.

In one embodiment, the CTS tool measures the duration of transmission of a clock signal across the plurality of clock lines to the group of clocked components and optimizes the clock tree as a function of the duration of the clock signal propagation and a duration for propagation of a data signal within a first component of the group of components that transmits the data signal to a second component of the group. Based on the evaluation, the tool selects a particular first clocked-component from a library that satisfies the criteria that the duration of propagation of the clock signal through the clock tree to a second component is faster in relation to the duration of propagation of the data signal from the first component triggered by receipt of the clock signal.

The method of FIG. 5 includes obtaining an integrated circuit design for analysis (100). The circuit may be in the form of representations of the components (devices and interconnects) of the design which, when manufactured in the corresponding layers of materials, will ensure the intended functioning of the components—this may include a netlist as described above. A group of clocked components that are to be driven by the same gated clock signal is identified (102).

In accordance with an embodiment of the disclosure, a goal for the design of the IC may include reducing the current consumption of the IC. Design criteria for achieving this goal may include reducing the size of the clock tree by reducing the size and number of clock tree delay elements placed across selected lines of the clock tree while effectively impacting the clock signal arrival to the clocked components of the IC. Among other things, the size and number of clock tree delay elements placed on a given clock line that propagates the clock signal to a receiving clocked component (e.g., 58*b*) is based on the timing properties of a transmitting clocked component (e.g., 58*a*) that provides a data signal propagated to the receiving clocked component. The timing properties of the transmitting clocked component include the duration of propagation of the data signal within the transmitting clocked component (e.g., clock-to-Q path delay in a flip-flop). As such, a first transmitting clocked component that provides a data signal to a receiving clocked component among the group of clocked components is identified (104).

Thereafter, a first duration corresponding to the propagation duration of a clock signal from a clock input pin of the IC to the first transmitting clocked component is measured (106). A second duration corresponding to a data signal propagation duration across a transmission path (e.g., clock-to-Q path in a flip-flop) of the first transmitting clocked component is measured (108). In alternate embodiments, the second duration may include a measurement of the duration of propagation of the data signal from a data output terminal of the first transmitting clocked component to a data input terminal of the second clocked component. A third duration corresponding to a propagation duration of the clock signal from the clock input pin of the IC to the second clocked component is measured (110).

In accordance with embodiments of this disclosure, optimization of the clock tree involves designing the signal paths of the clock lines and the clocked component data propagation to ensure that the clock signal arrives at the second clocked component prior to receipt of the data signal from the first transmitting clocked component. As such a comparison is performed of the third duration against the first duration only or the sum of the first and second durations (112). In another example, the third duration may be compared against only the second duration. The premise for such a comparison is that provided the data signal takes longer to propagate from an output of the transmitting clocked component to the input of the receiving clocked component, relative to the propagation duration of the clock signal, the circuit design will function as expected. In response to performing the comparison, the method determines whether the comparison yields a result indicating that the third duration is shorter in comparison to either the second duration only, or the sum of the first and second durations (114) for a given transmitting component.

In response to determining that the third duration is longer than the sum of the first and second durations, a second transmitting clocked component is selected that has a slower transmission speed (in relation to the first transmitting clocked component) of data within the clocked component (116). A slower transmission path may be achieved by providing the second transmitting clocked component that includes a clocked component delay element having a greater capacity in comparison to the clocked component delay element in the first transmitting clocked component. As discussed previously, the increased capacity may be achieved by, for example, coupling additional clocked component delay elements, or varying the size of the clocked component delay elements to lengthen the transmission duration of data propagation within the first transmitting clocked component. The clocked component delay elements may include inverters or buffers comprised, for example, of transistors, or transistors coupled as load elements. As a consequence of selecting a slower second transmitting clocked component, the clock tree can be reduced in size and this size reduction contributes to a reduction in the current consumption by the IC and effectively by the IMD 20. The inventors have theorized that a transmitting clocked component that has a transmission path with, for example, a first order of magnitude slower transmission path may yield at least as much as a four time (4×) factor decrease in the size or number of clocked component delay elements that would otherwise be required if the CTS tool were to insert clock tree delay elements in the clock line in accordance with conventional practice.

Upon achieving a design whereby the selected second transmitting clocked component satisfies the criteria that the third duration is shorter than the sum of the first and second durations, the analyzed IC design is converted into a representation of a physical design that is fabricated into a three dimensional integrated circuit chip (118). The representation of the physical design may be in the form of a modified netlist or a partial schematic which may be stored in a memory of the CTS tool and subsequently integrated into a complete layout for the fabrication process to create the IC. In yet another embodiment, the physical design representation may include the timing constraints for the transmission path of a data signal within the second transmitting clocked component. The timing constraints may subsequently be utilized to modify the internal-structure design of the transmitting clocked component or to select an appropriate clocked component.

Although not illustrated in the figures, tasks 104 through 112 may be repeated in yet another embodiment of the method of FIG. 5 for all the clocked components identified at task 102. Such a comparison may find implementation in low power device designs that utilize sub-micron process technologies and that are not speed constrained, including implantable medical devices. In such devices, a library of clocked components may also be designed to satisfy the timing requirements for the slowest component without impacting the circuit's functionality. In that example embodiment, a task may be performed to determine the slowest second duration. The second duration would therefore be used as the basis for the design of all the clocked components in the circuit which would reduce the complexity of the clock tree. Accordingly, the method utilizes the slowest identified second duration for performing tasks 114-118 to define the clocked component delay element specifications at task 118.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An integrated circuit, comprising:
   a clock source for generating a clock signal;
   a clock tree having a plurality of clock lines distributed within the integrated circuit for transmission of the clock signal;
   a plurality of clocked components, wherein each of the clocked components includes a data signal transmission path having a clocked component delay element and being connected to one of the plurality of clock lines;
   a first data signal line coupled between a data output of a transmitting clocked component of the plurality of clocked components and a data input of a receiving clocked component of the plurality of clocked components; and
   a clock tree delay element coupled to a clock line of the receiving clocked component to generate a modified clock signal, wherein the transmitting clocked component is configured to output the data subsequent to reception of the modified clock signal by the receiving clocked component, and
   wherein each of the plurality of clocked components comprises a flip-flop, and the data signal transmission path of each of the plurality of clocked components is defined between an input terminal and an output terminal of each flip-flop.

2. The integrated circuit of claim 1, wherein the clocked component delay element of the configured transmitting clocked component yields a predetermined duration of propagation of the data across the data signal transmission path.

3. The integrated circuit of claim 2, wherein the clocked component delay element of the configured transmitting clocked component provides a combined duration of data propagation and transmission of the clock signal to the transmitting clocked component that is greater relative to a duration of transmission of the modified clock signal to the receiving clocked component.

4. The integrated circuit of claim 1, wherein the transmission path of the transmitting clocked component is configured based on a duration of the transmission of the clock signal to the transmitting clocked component and a duration of the transmission of the modified clock signal to the receiving clocked component.

5. The integrated circuit of claim 4, wherein the configured transmitting clocked component includes a predefined clocked component delay element that provides a combined duration of data propagation and transmission of the clock signal to the transmitting clocked component that is greater relative to a duration of transmission of the modified clock signal to the receiving clocked component.

6. The integrated circuit of claim 1, wherein the transmission path of the transmitting clocked component is configured by modifying a capacity of the clocked component delay element.

7. The integrated circuit of claim 6, wherein the capacity of the clocked component delay element is modified to provide a greater duration of the transmission of the data signal within the transmitting clocked component to control the propagation speed of the data signal for receipt by the receiving clocked component subsequent to receipt by the receiving clocked component of the modified clock signal.

8. The integrated circuit of claim 1, wherein the transmission path of the transmitting clocked component is configured by increasing a capacity of the clocked component delay element, wherein the capacity is increased by one of increasing the size of the clocked component delay element and increasing the number of stages of the clocked component delay element.

9. The integrated circuit of claim 8, wherein the clocked component delay element comprises at least two transistors.

10. The integrated circuit of claim 1, further comprising:
   a third clocked component of the plurality of clocked components; and
   a second data signal line coupled between a data output of the receiving clocked component and a data input of the third clocked component, wherein the receiving clocked component is configured having a second clocked component delay element coupled to a second data signal transmission path within the receiving clocked component and the second clocked component delay element is configured as a function of transmission of the clock signal to the third clocked component.

11. The integrated circuit of claim 1, wherein the plurality of clocked components comprise a flip-flop.

12. An implantable medical device having an integrated circuit for controlling a therapy delivery and a sensing function comprising:
   a clock source for generating a clock signal;
   a clock tree having a plurality of clock lines distributed within the integrated circuit for transmission of the clock signal;
   a plurality of clocked components, wherein each of the clocked components includes a data signal transmission path having a clocked component delay element and being connected to one of the plurality of clock lines;
   a first data signal line coupled between a data output of a transmitting clocked component of the plurality of clocked components and a data input of a receiving clocked component of the plurality of clocked components; and
   a clock tree delay element coupled to a clock line of the receiving clocked component to generate a modified clock signal, wherein the transmitting clocked component is configured to output the data subsequent to reception of the modified clock signal by the receiving clocked component, and
   wherein each of the plurality of clocked components comprises a flip-flop, and the data signal transmission path of each of the plurality of clocked components is defined between an input terminal and an output terminal of each flip-flop.

13. The implantable medical device of claim 12, wherein the transmitting clocked component is configured based on a duration of the transmission of the clock signal to the transmitting clocked component and a duration of the transmission of the modified clock signal to the receiving clocked component.

14. The implantable medical device of claim 12, wherein configuring the transmitting clocked component comprises modifying a capacity of the clocked component delay element to extend a propagation interval of the data along a transmission path of the transmitting clocked component.

15. The implantable medical device of claim 14, wherein modifying the capacity of the clocked component delay element of the transmitting clocked component comprises one of increasing the size of the clocked component delay element and increasing the number of stages of the clocked component delay element.

16. A method of optimizing power consumption in an integrated circuit, comprising:
   transmitting a clock signal through a clock tree having a plurality of clock lines, wherein each of the clock lines is coupled to a plurality of clocked components;
   configuring a first of the plurality of clocked components as a transmitting clocked component coupled to a first of the plurality of clock lines;
   propagating a clock signal to the transmitting clocked component through the first clock line;
   measuring a duration of propagation of the clock signal to the transmitting clocked component;
   propagating the clock signal through a clock tree delay element coupled to a second of the plurality of clock lines to provide a modified clock signal to a first of the plurality of clocked components that is configured as a receiving clocked component;
   measuring a duration of transmission of the modified clock signal to the receiving clocked component;
   generating a data signal at the transmitting clocked component in response to receipt of the clock signal by the receiving clocked component; and
   transmitting the data signal from the transmitting clocked component to the receiving clocked component,
   wherein configuring the transmitting clocked component comprises providing a data transmission path within the transmitting clocked component having a clocked component delay element that yields a predetermined propagation duration of the data that results in receipt of the data signal by the receiving clocked component subsequent to receipt of the modified clock signal, and
   wherein the transmitting clocked component comprises a flip-flop, and the data transmission path provided within the transmitting clocked component is defined between an input terminal and an output terminal of the flip-flop.

17. The method of claim 16, further comprising obtaining an interval between a reception of the modified clock signal by the receiving clocked component and a reception of the data signal transmitted from the transmitting clocked component to the receiving clocked component.

18. The method of claim 16, wherein the transmission path provides a predetermined interval between the reception of the clock signal at the transmitting clocked component and the reception of the data signal by the receiving clocked component.

19. The method of claim 16, wherein the transmission path is coupled to a clocked component delay element having a capacity to yield the predetermined propagation duration of the data.

20. The method of claim 16, wherein configuring the transmitting clocked component comprises selecting a clocked component from a library including a plurality of clocked components having clocked component delay elements with varied capacities.

21. The method of claim 16, wherein the predetermined propagation duration of the data comprises the duration of transmission of the modified clock signal to the receiving clocked component being larger in comparison to the combined duration of transmission of the clock signal to the transmitting clocked component and the duration of propagation of the data signal from the transmitting clocked component to the receiving clocked component.

22. An integrated circuit, comprising:
a clock source for generating a clock signal;
a clock tree having a first clock line and a second clock line, the first and second clock lines being coupled to the clock source for transmission of the clock signal;
a first flip-flop having a data signal transmission path defined between an input terminal and an output terminal, the signal transmission path having a clocked component delay element and the first flip-flop being connected to the first clock line;
a second flip-flop coupled to the second clock line;
a first data signal line coupled between the output terminal of the first flip-flop and an input terminal of the second flip-flop; and
a clock tree delay element coupled to the second clock line to generate a modified clock signal, wherein the clocked component delay element of the first flip-flop is configured to propagate data through the data signal transmission path for output of the data at the output terminal subsequent to reception of the modified clock signal by the second flip-flop.

\* \* \* \* \*